(12) United States Patent
Gabbard et al.

(10) Patent No.: US 6,186,997 B1
(45) Date of Patent: *Feb. 13, 2001

(54) MULTIPLE USE UNIVERSAL CONNECTOR

(75) Inventors: Mark E. Gabbard, Salisbury, MD (US); John J. Niedospial, Jr., Burlington, NJ (US); Timothy J. Gabbard, Salisbury, MD (US)

(73) Assignee: Bracco Research USA, Priceton, NJ (US)

( * ) Notice: Under 35 U.S.C. 154(b), the term of this patent shall be extended for 0 days.

This patent is subject to a terminal disclaimer.

(21) Appl. No.: 09/119,470

(22) Filed: Jul. 20, 1998

Related U.S. Application Data

(63) Continuation-in-part of application No. 09/009,487, filed on Jan. 20, 1998, now Pat. No. 6,019,751.

(51) Int. Cl.⁷ ...................................................... A61B 19/00
(52) U.S. Cl. ........................ 604/408; 604/415; 215/247; 206/828
(58) Field of Search ..................................... 604/403, 408, 604/411–415; 215/247, 249; 206/828

(56) References Cited

U.S. PATENT DOCUMENTS

| | | | |
|---|---|---|---|
| 2,364,126 | * 12/1944 | Cantor et al. | 604/415 |
| 4,084,718 | * 4/1978 | Wadsworth | 215/247 |
| 4,312,349 | * 1/1982 | Cohen | 604/415 |
| 4,838,875 | * 6/1989 | Somor | 604/408 |
| 5,071,413 | 12/1991 | Utterberg . | |
| 5,360,413 | 11/1994 | Leasont et al. . | |
| 5,391,150 | 2/1995 | Richmond . | |
| 5,540,674 | * 7/1996 | Karas et al. | 604/415 |
| 5,573,516 | 11/1996 | Tyner . | |

* cited by examiner

Primary Examiner—Dennis Ruhl
(74) Attorney, Agent, or Firm—Imre Balogh

(57) ABSTRACT

Multiple use universal connector designed for use in various containers having a fluid port for accessing to the content of the container or for transferring fluid into the container. The multiple use universal connector incorporates a diaphragm capable of being penetrated repeatedly by an access means such as a luer connector or a syringe having a sharp or blunt cannula for fluid communication between the content of the container and the access means. The multiple use universal connector re-seals itself after being penetrated and the access means removed therefrom.

10 Claims, 13 Drawing Sheets

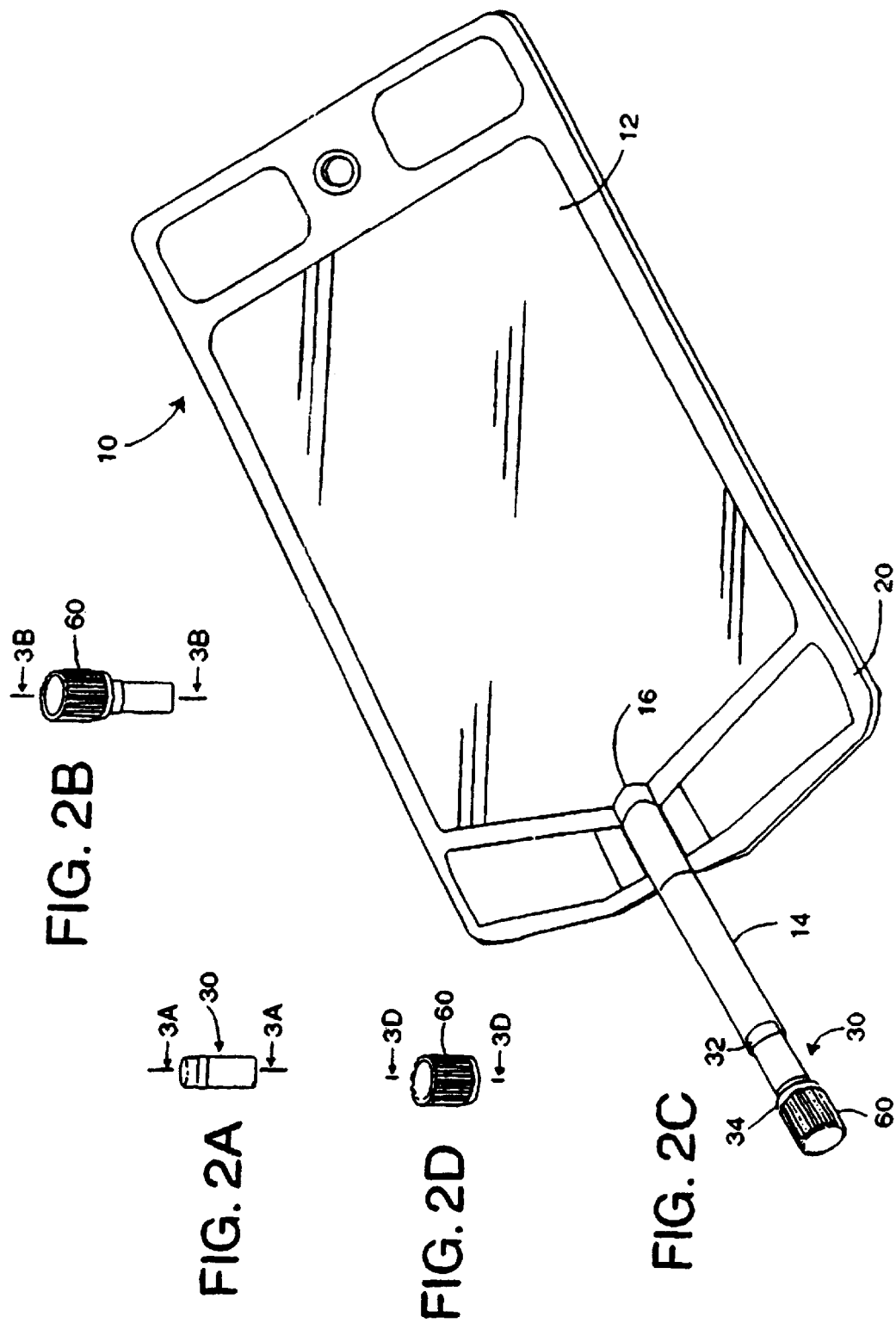

MULTIPLE USE UNIVERSAL CONNECTOR

This application is a continuation-in-part of application Ser. No. 09/009,487, filed on Jan. 20, 1998 now U.S. Pat. No. 6,019,751.

BACKGROUND OF THE INVENTION

1. Field of the Invention

This invention relates to a universal connector connectable to containers having fluid contents therein designed for delivery to a site of administration. More particularly, the invention relates to a universal connector having a self-sealing means so that a pharmaceutical fluid contained in a container closed by the universal connector can be repeatedly accessed.

2. Reported Developments

Parenteral fluids, such as therapeutic drugs, diagnostic contrast media and nutrients are conventionally administered to a patient from a container, such as a collapsible bag or bottle having a fluid exit port. The fluid exit port may include means, such as a tube, spike or cannula, the distal end of which is in communication with the fluid content of the container and the proximal end of which is connected to the desired site on the patient. Conventionally, the proximal end of said means includes a needle that can puncture the patient. The fluid exit port is sealed by a membrane which is punctured by inserting a spike into the exit port when fluid delivery is desired.

One approach used by the prior art to penetrate the membrane covering the fluid exit port comprises the use of syringes or spikes which carry the danger of accidental injuries caused by the sharp points of the needles and spikes. Such injuries accidentally inflicted on the health practitioner carry the further risk of getting infected with diseases such as AIDS. In order to reduce the danger of accidental injuries, spikes having relatively blunt tips were used. However, such spikes puncture a large area of the membrane and once the spikes are removed the membrane no longer seals the fluid exit port.

Another approach used by the prior art is the provision of a tubular member which is more blunt than a spike so that it is unlikely to penetrate the skin yet capable of penetrating the latex diaphragm type seals.

Still another approach used by the prior art is a valve positioned in the fluid exit port, the valve being operable by engagement with a spikeless or needleless IV component and contains a resilient valve disc positioned in the fluid passageway and blocks fluid flow when the disc is in the closed position, and allows fluid flow when the disc is in the open position.

Still another needleless connector of the prior art uses a resilient conical valve head in a housing. The conical valve head is positioned against the valve seat to form a seal. When the male fitting of a syringe, or some other device, is inserted into the inlet of the housing, it pushes the tip portion of the resilient valve head inwardly so that the valve head is deformed away from the valve seat thereby allowing fluid communication. In still other embodiments of the prior art, a needleless connector includes an elastomeric conical valve head biased against a conical valve seat by a helical spring to form a seal.

The above generally described devices have greatly reduced the use of syringes to withdraw medical fluids from collapsible bags and bottles thereby reducing needle-stick injuries and associated risks. The devices also advanced the prior art by providing convenient connectors which can be easily connected to the containers of medical fluids.

However, there still exists the need to provide a universal connector which may be used with a wide variety of connection sites. A seal or diaphragm is a main component of the herein-described invention which does not require penetration by any sharp or even blunt object in order to establish fluid communication between the content of the container and the site of delivery. The seal or diaphragm serves as access means and provides for hermetic sealing, safe handling, sterilization and storing. The seal or diaphragm is designed for multiple use so that the medical fluid can be accessed repeatedly. After each withdrawal of the desired amount of the medical fluid, the seal or diaphragm self-seals itself thereby preventing contamination of the medical fluid by air-born particles such as dust and bacteria.

SUMMARY OF THE INVENTION

In accordance with the present invention there is provided a multiple use universal connector which can be used to repeatedly access the fluid content of a container or to repeatedly transfer a fluid into the container. The multiple use universal connector can be used in collapsible and non-collapsible bags, bottles and vials made of glass or polymeric material which contain a fluid exit port into which the universal connector is inserted sealing the fluid exit port. The fluid contained in the container may be a therapeutic liquid, diagnostic media or a nutritional formula which can be sterilized in bulk and then aseptically transferred into the container or it can be sterilized in the container stoppered with the universal connector. The multiple use universal connector is made of rigid or semi-rigid polymeric materials such as polyvinyl chloride, polyethylene and polypropylene.

The fluid in a container stoppered by the multiple use universal connector can be accessed by means well-known in the art, such as syringes having sharp or blunt needle cannulas. Preferably, the access means comprises a luer connector in order to prevent accidental injuries to health care workers and patients caused by the use of syringes.

The multiple use universal connector comprises:

(1) a connector body of tube-like configuration the distal end of which is designed to be slideably insertable into the fluid exit port, and the proximal end of which is designed to seal the content of the container by an elastomeric membrane and also to receive a removable cap; and (2) a removable cap threaded onto the proximal end of the connector which, prior to use, is removed so that the content of the container could be accessed by the use of a luer connector having a configuration that is similar to the configuration of the cap or by other access means, such as sharp or blunt needle cannulas.

The elastomeric membrane sealing the proximal end of the universal connector is of an inert, gas-impermeable polymeric material capable of flexing under internal or external pressures such as exerted thereon during steam sterilization. It preferably has a thickness of from about 0.001 mm to about 1.00 mm and a durometer of from about 25 to about 80 Shore A. It is capable of being ruptured by the twisting motion of a blunt luer connector or syringes having sharp or blunt needle cannula. The configuration of the elastomeric membrane is M-shaped having vertical leg portions and a top surface resembling a cup shape.

The tube-like body of the universal connector further comprises: first cap-locking ring on the proximal end of the body which serves as a male thread to receive the removable cap; and second cap-locking ring spaced from the first cap-locking ring towards the distal end of the tube-like body, which serves as stopping means for the cap when the cap is threaded onto the tube-like body of the universal connector.

BRIEF DESCRIPTION OF THE DRAWINGS

In the drawings, like numerals indicate like elements and primes (') indicate counterparts of like elements.

FIG. 2A is a perspective view of the multiple use universal connector of the present invention without the cap attached;

FIG. 2B is a perspective view of the multiple use universal connector of the present invention with the cap attached;

FIG. 2C is a perspective view of the multiple use universal connector of the present invention with the cap attached and connected to the medical bag of FIG. 1;

FIG. 2D is a perspective view of the cap;

DETAILED DESCRIPTION OF THE INVENTION

Figure 1:
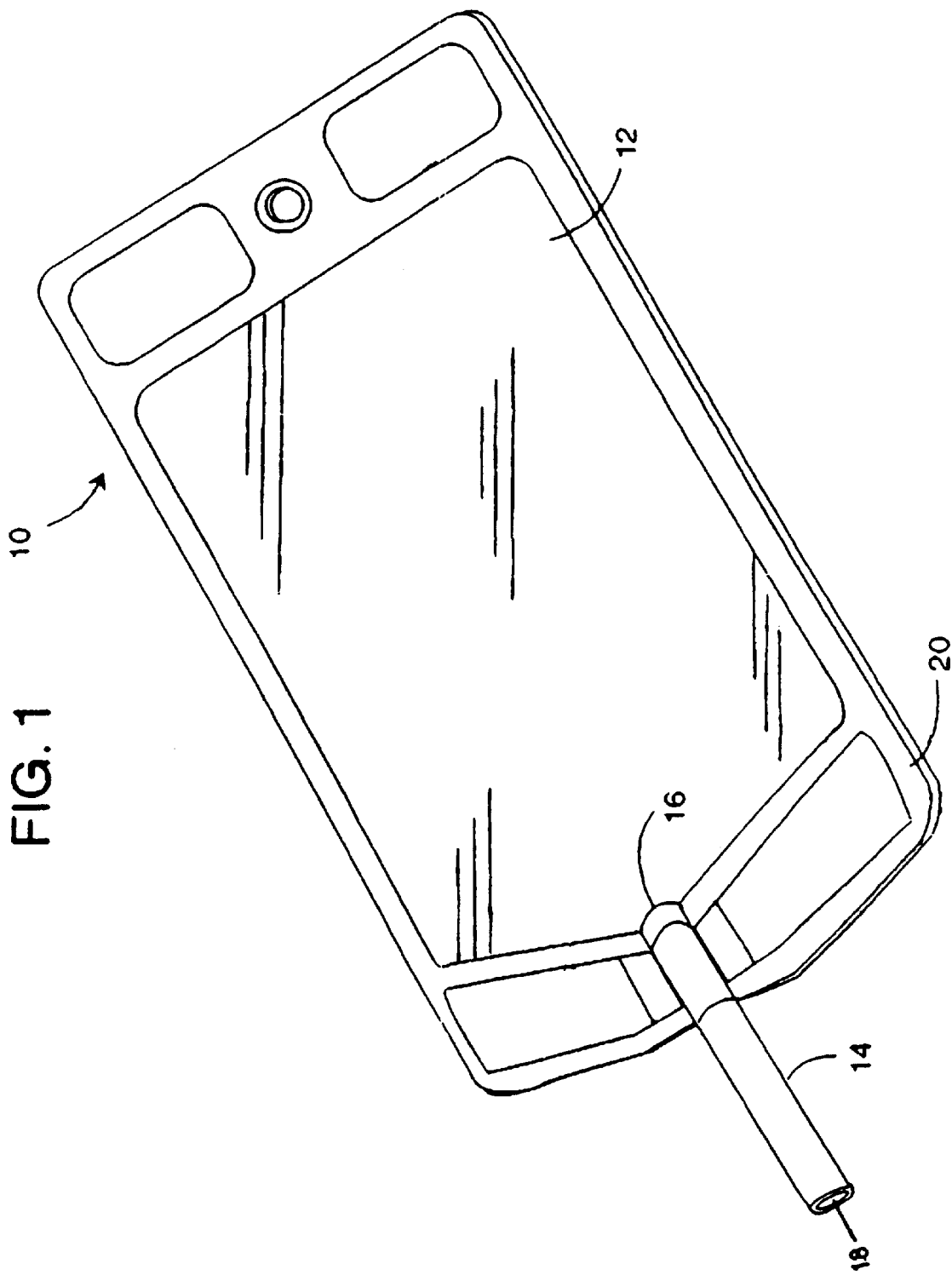
FIG. 1 is a prospective view of a medical bag.

Referring to FIGS. 1, 2A, 2B, 2C and 2D, there is shown an intravenous bag 10 of conventional generally rectangular configuration made of inert, flexible, polymeric material such as polyvinylchloride. The multiple use universal connector of the present invention will be described in reference to such flexible, polymeric bags, however, the multiple use universal connector can be used with other fluid containers such as bottles and vials of various configurations made of rigid or semi-rigid materials. Such containers will have fluid exit ports into which the universal connector can slideably be attached or it can be an integral part thereof. The IV bag 10 contains a medical fluid 12 therein, such as a therapeutic, diagnostic or nutritional preparation. The medical fluid 12 may be pre-sterilized in bulk prior to its transfer to the IV bag, or it may be sterilized in the IV bag using sterilizing equipment and techniques known in the art. The IV bag further comprises a fluid exit port or tube 14 the distal end 16 of which is in communication with medical fluid 12 and the proximal end 18 of which is to slideably receive distal end 32 of multiple use universal connector 30. Alternatively, multiple use universal connector 30 may be integral with fluid exit port or tube 14 of IV bag 10. In both cases, fluid exit port or tube 14 is sealed into IV bag 10 by bottom seam 20 of IV bag 10. On the proximal end 34 of multiple use universal connector 30, cap 60 is mounted having internal thread means thereon for enclosing said proximal end 34. Prior to use, cap 60 is removed from multiple use universal connector 30 for engagement with a luer connector.

FIG. 2A shows the multiple use universal connector without the cap; FIG. 2B shows the multiple use universal connector with the cap; and FIG. 2D shows the cap, all views being shown in perspective.

Reference is now being made to FIGS. 3A, 3B, 3C, 4A and 4B.

Figure 3A:
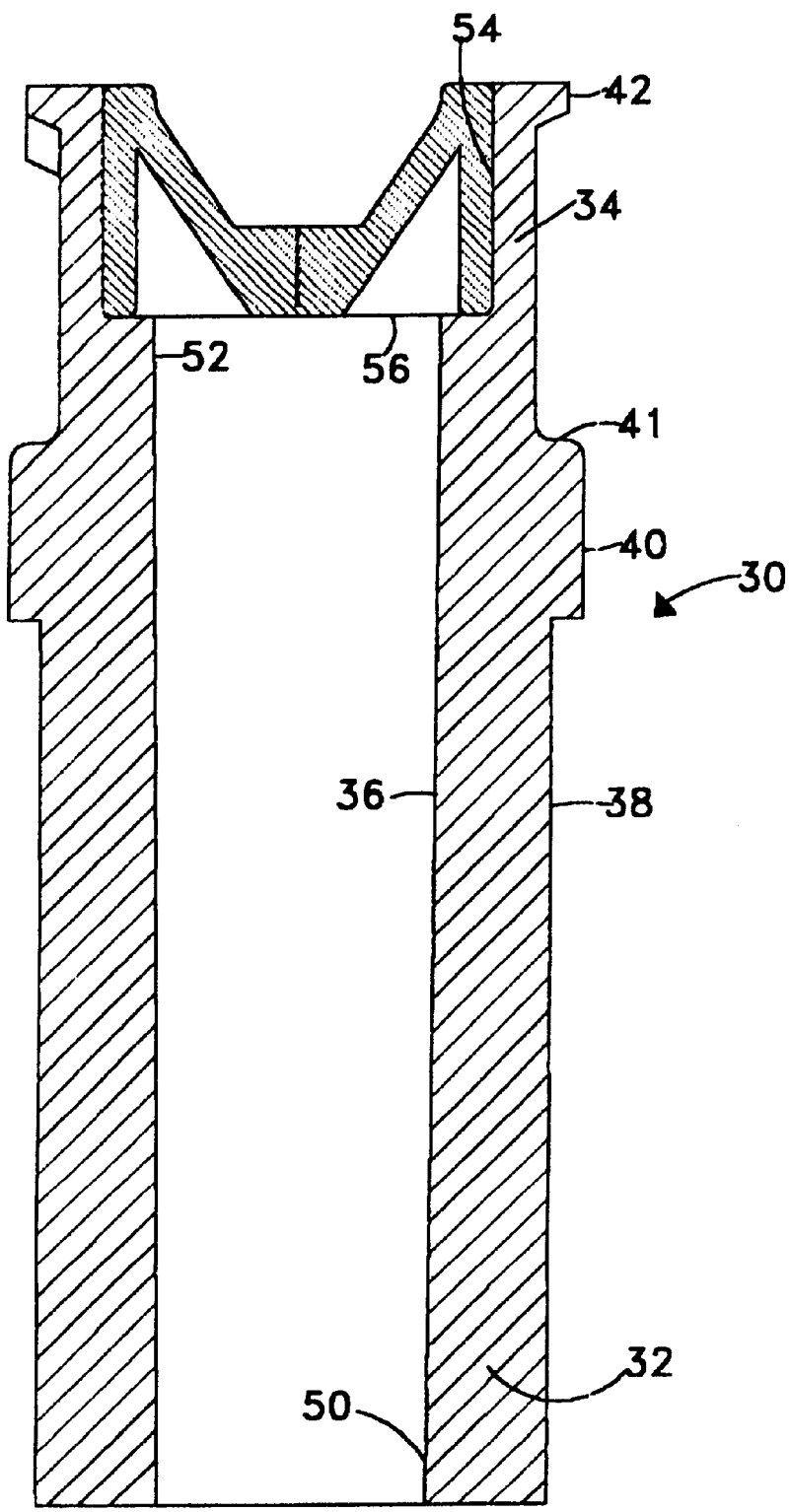
FIG. 3A is a cross-section of the multiple use universal connector without the cap attached taken along the line 3A—3A of FIG. 2A.

FIG. 3A shows a cross-sectional view of the multiple use universal connector without the cap taken along the line 3A—3A of FIG. 2A.

Figure 3B:
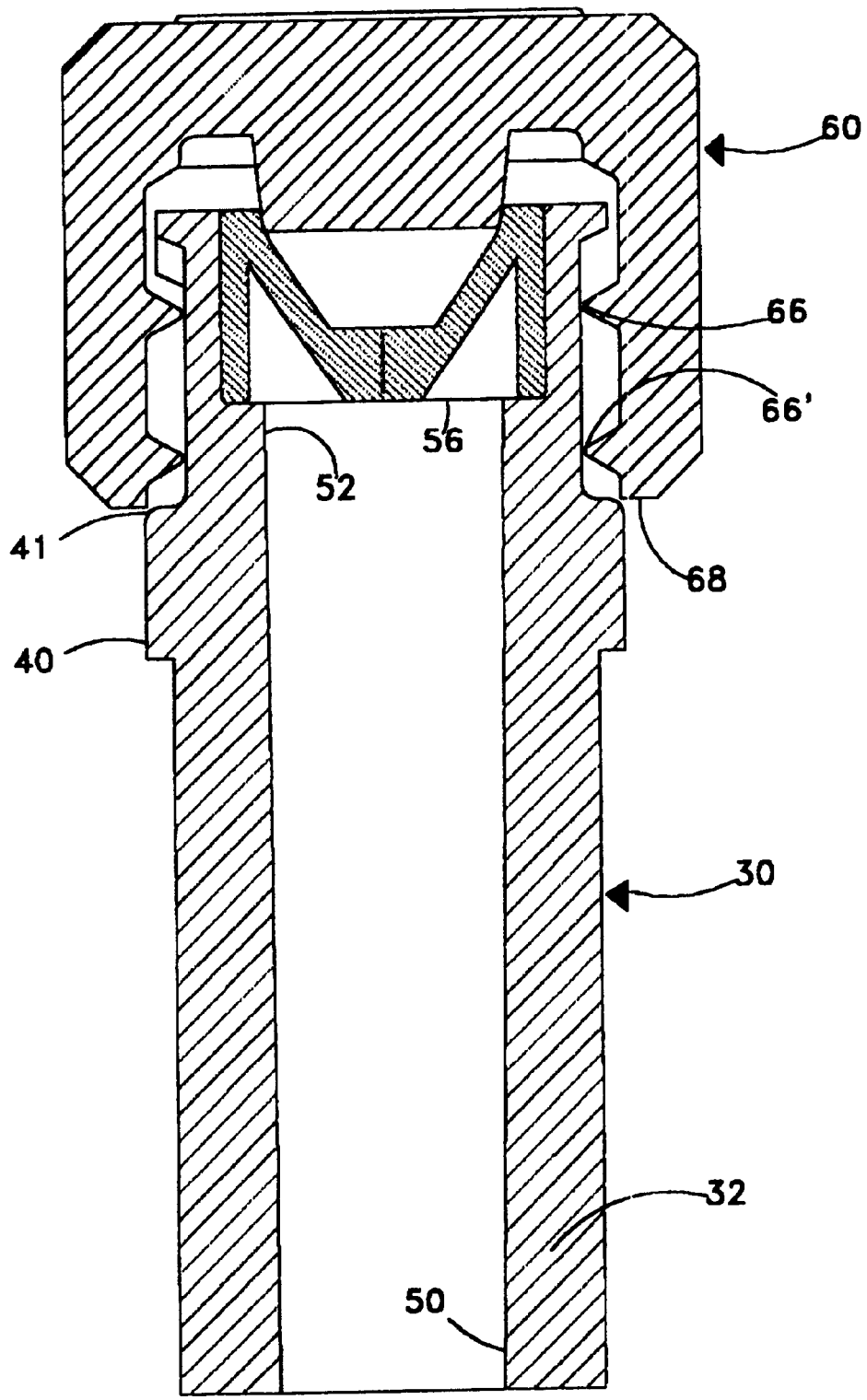
FIG. 3B is a cross-section of the multiple use universal connector with the cap attached taken along the line 3B—3B of FIG. 2B.

FIG. 3B shows the universal connector assembly taken along the line 3B—3B of FIG. 2B.

Figure 3C:
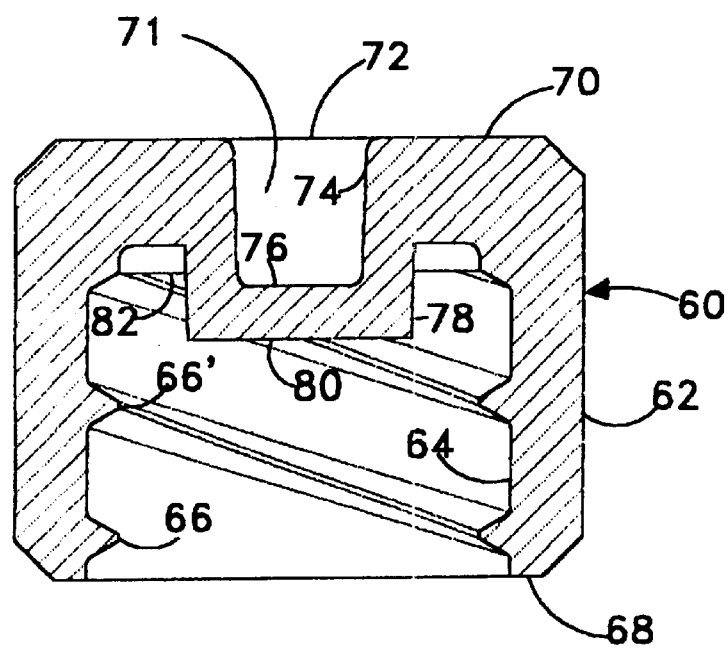
FIG. 3C is a cross-section of the cap taken along the line 3D—3D of FIG. 2D.
Figure 3D:
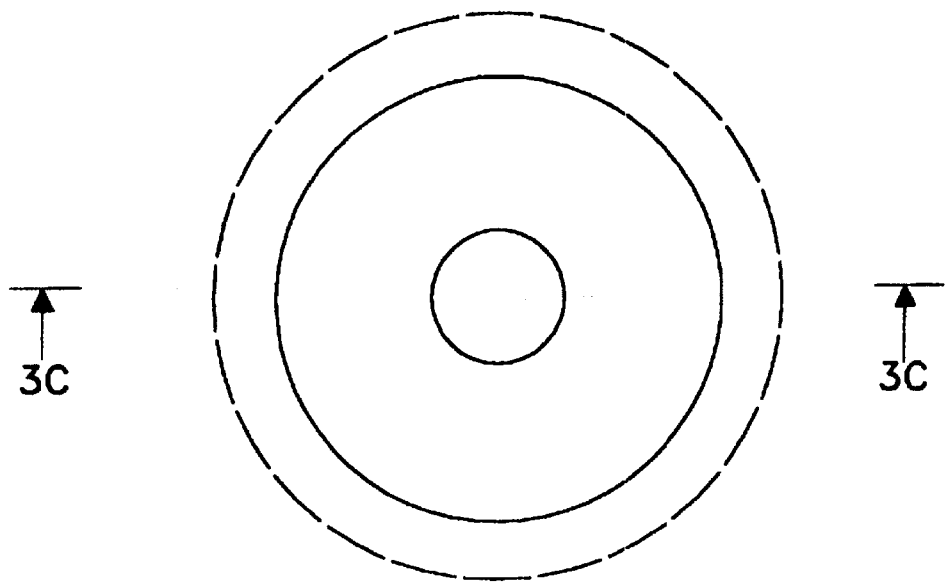
FIG. 3D is a top plan view of the cap shown in FIG. 2D.

FIG. 3C shows a cross-section of the cap taken along the line 3D—3D of FIG. 2D, and FIG. 3D shows the top plan view thereof.

The multiple use universal connector 30 is of tube-like configuration comprising: distal end 32 and proximal end 34; inside wall 36 and outside wall 38. Integral part of outside wall 38 at the proximal end 34 thereof is positioned first cap-locking ring 40 spaced from second cap-locking ring 42. First cap-locking ring serves as a male thread to receive cap 60 and to engage its internal threads 66 and 66'. Second cap-locking ring 42 having proximal end 41 has a larger external diameter than the distance defined by a line connecting internal threads 66–66' located at the proximal end 68 of cap 60. Second cap locking-ring 42 serves as stopping means for cap 60 when cap 60 is threaded onto the multiple use universal connector 30.

Inside wall 36 of multiple use universal connector 30 comprises: a distal end 50 and proximal end 52. Distal end 50 is designed to slideably and sealingly engage fluid exit port or tube 14 to slide into the fluid exit port through its proximal end 18.

At the proximal end 52 of multiple use universal connector 30 a cylindrical opening is defined by side wall 54 and bottom wall 56. The cylindrical opening is designed to receive cylindrical protuberance defined by outside walls 78 and 80 of cap 60.

Figure 4A:
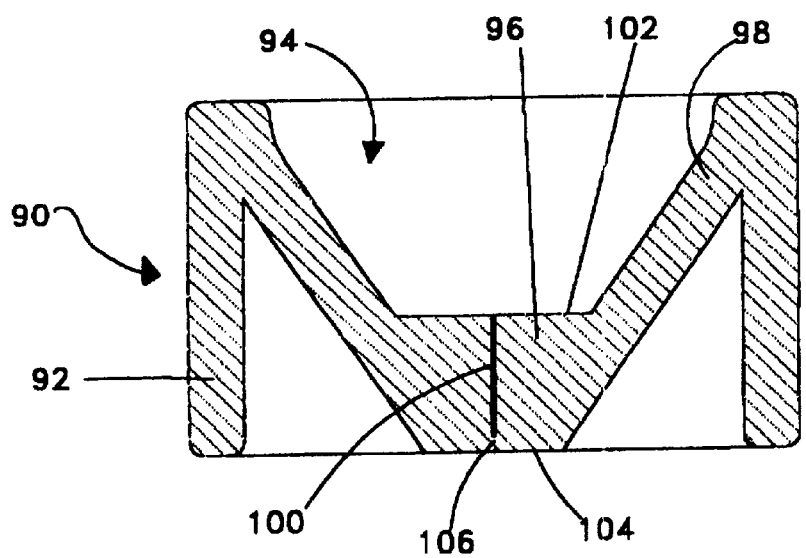
FIG. 4A is a greatly enlarged cross-section of the M-shaped diaphragm shown in FIG. 3A.

Bottom wall 56 and side wall 54 of cylindrical opening in multiple use universal connector 30, as best seen in FIG. 3B and FIG. 4A, contain an elastomeric diaphragm 90 bonded to the universal connector. The elastomeric diaphragm is of an M-shaped configuration and seals the fluid channel defined by the proximal end of inside wall 52 of universal connector 30. The diaphragm is of inert gas-impermeable polymeric material capable of flexing under internal or external pressures such as exerted during steam sterilization. The diaphragm has a durometer of from about 25 to about 80 Shore A. Suitable elastomeric materials for constructing the diaphragm include:

natural rubber;

acrylate-butadiene rubber;

cis-polybutadiene;

chlorobutyl rubber;

chlorinated polyethylene elastomers;

polyalkylene oxide polymers;

ethylene vinyl acetate;

fluorosilicone rubbers;

hexafluoropropylene-vinylidene fluoride-tetrafluoroethylene terpolymers, such as sold under the tradenames of Fluorel amd Viton;

butyl rubbers;

polyisobutene, such as sold under the tradename Vistanex;

synthetic polyisoprene rubber;

silicone rubbers;

styrene-butadiene rubbers;

tetrafluoroethylene propylene copolymers; and thermoplastic-copolyesters.

Figure 4B:
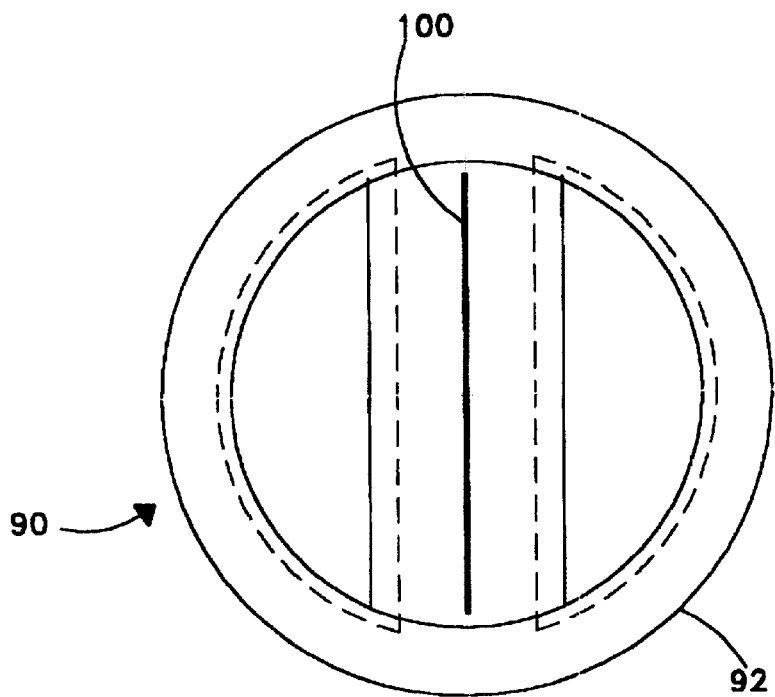
FIG. 4B is a top plan view of the M-shaped diaphragm shown in FIG. 4A.

As best seen in FIGS. 4A and 4B, M-shaped diaphragm 90 comprises leg portion 92 and cup-shaped portion 94. Cup-shaped portion comprises:

a horizontal bottom portion 96; and side portion 98 which enclose an obtuse angle between them. Leg portion 92 and side portion 98 typically have a thickness of from about 0.1 to 6 mm, while bottom portion 96 typically has a thickness of from about 1 to 20 mm.

The horizontal bottom portion 96 is provided with a slit 100 which extends from the top surface 102 of the horizontal bottom portion toward the bottom surface 104. However, the slit does not penetrate the bottom surface. The unpenetrated membrane, denoted by the numeral 106, is typically of from about 0.001 mm to about 2.0 mm. The unpenetrated membrane maintains the content of the container, in which the multiple use universal connector is used, in sealed condition. In use, when this membrane is ruptured by an external access means, such as a needle cannula, luer connector or spike, fluid communication is established between the content of the container and the external access means. Upon disengaging the external access means for the multiple use universal connector, the cup-shaped portion of the diaphragm reseals itself for the reason that the membrane is resilient and springs back to its original configuration. As a result the container is resealed until the fluid withdrawal process is repeated.

As best seen in FIGS. 3C and 3D, cap 60 is designed for securely closing multiple use universal connector 30 at the proximal end 34 thereof, and protecting elastomeric diaphragm 90 from contact with the outside environment. The configuration of the cap closely approximates the luer connector shown in FIG. 6 which, in addition to the features detailed as the description of the cap proceeds, also contain a tubing conduit which is part of the luer connector. FIGS. 3C and 3D show cylindrical cap 60 comprising: outside wall 62 and inside wall 64. Outside wall 62 comprises: bottom wall 68; top wall 70; and central portion 72 of top wall 70. Inside wall 64 comprises: internal threads 66 and 66' extending towards the center of the cap; a cylindrical protuberance defined by outside wall 78 and bottom wall 80 extending distally into the space defined by the inside wall; and shoulder portion 82 connecting inside wall 64 and outside wall 78 of the cylindrical protuberance. In the proximal end of cap 60 there is located plug 71 defined by central portion 72 of top wall 70, and bottom wall 76. Plug 71 may be integral with the cap such as obtained by blow molding technique or the plug may be manufactured separately and subsequently sealed into the cap.

Referring again to FIGS. 3B and 3C, when cap 60 is threaded onto universal multiple use connector 30, bottom wall of protuberance 80 will be spaced from elastomeric diaphragm 90 allowing the membrane to flex outward under pressure, such as created during heat sterilization. However, spacing should not be more than about 0.1 to 3 mm so that under accidentally high pressures bursting of the membrane is prevented by the support of bottom wall 80 of cylindrical protuberance.

Figure 5A:
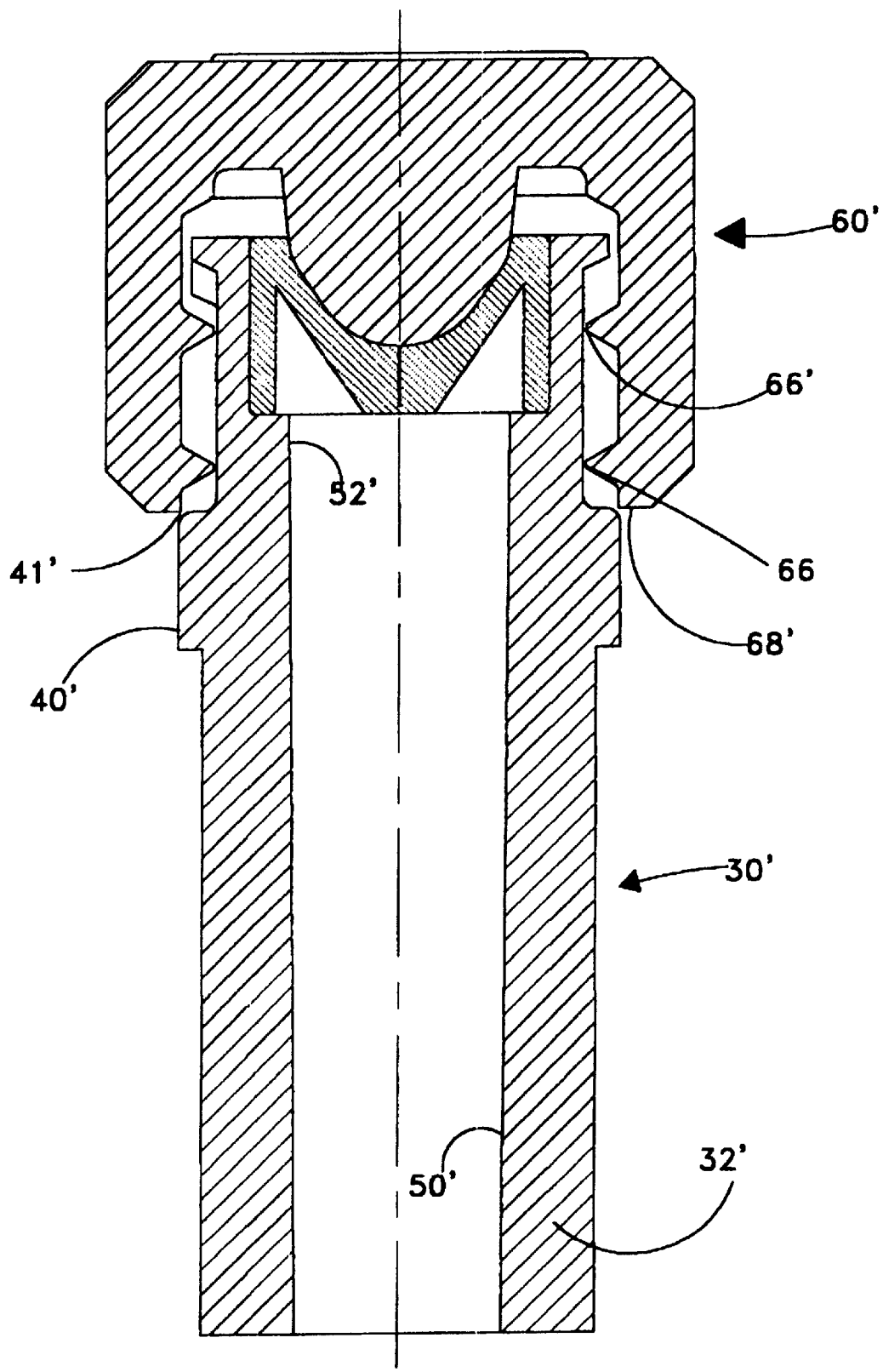
FIG. 5A is a cross-sectional view of another embodiment of the multiple use universal connector with the cap attached, wherein the M-shaped diaphragm has a smooth, semi-circular top surface.
Figure 5B:
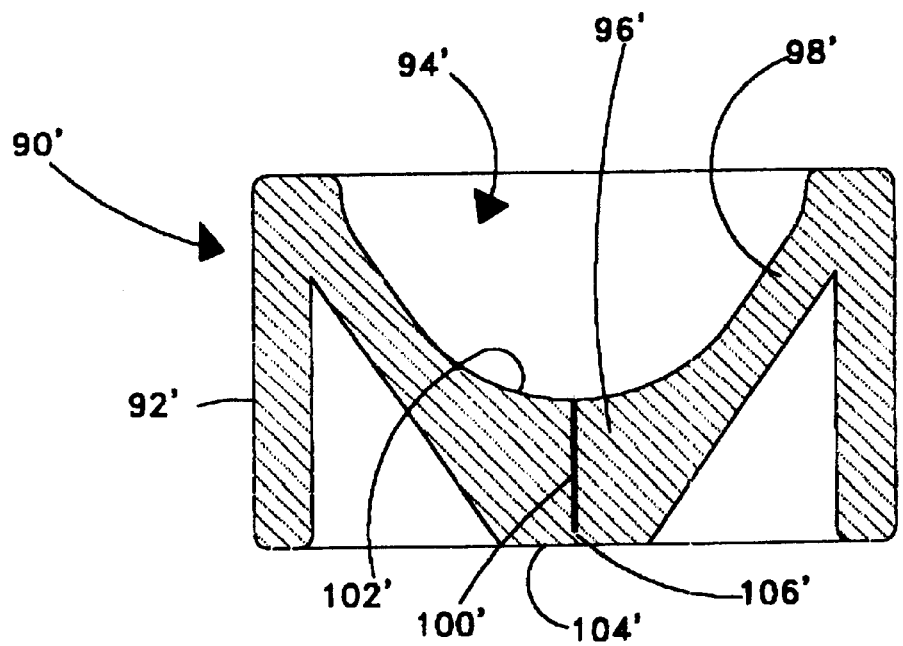
FIG. 5B is a greatly enlarged cross-section of the M-shaped diaphragm shown in FIG. 5A.
Figure 5C:
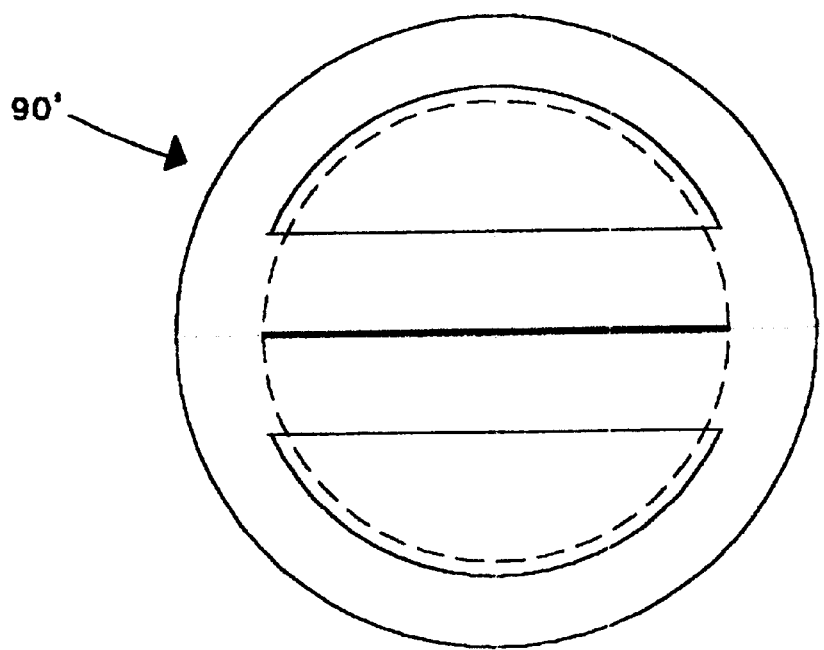
FIG. 5C is a top plan view of the M-shaped diaphragm shown in FIG. 5B.

FIGS. 5A, 5B and 5C show another embodiment of the multiple use universal connector of the present invention. FIG. 5A shows a cross-sectional view with the cap attached. FIG. 5B shows a cross-sectional view of an M-shaped diaphragm and FIG. 5C shows a top plan view thereof. In these figures the numbers with prime (') denote the same parts as in FIGS. 3A, 3B, 3C, 3D, 4A and 4B. In this embodiment the M-shaped diaphragm 90' comprises: leg portion 92'; and cup-shaped portion 94'. Cup-shaped portion comprises: horizontal bottom portion 96'; and side portion 98' which enclose a semi-circular surface 102'. Leg portion 92' and side portion 98' typically have a thickness of from about 0.1 to 6 mm, while bottom proton 96' typically has a thickness of from about 1 to 20 mm.

The horizontal bottom portion 96' is provided with slit 100' which extends from the top semi-circular surface 102' of the horizontal bottom portion toward the bottom surface 104. However, the slit does not penetrate the bottom surface. The unpenetrated membrane, denoted by the numeral 106' is typically of from about 0.001 mm to about 2.0 mm. The unpenetrated membrane maintains the content of the container, in which the multiple use universal connector is used, in sealed condition.

In use, when this membrane is ruptured by an external access means, such as a needle cannula, luer connector or spike, fluid communication is established between the content of the container and the external access means. Upon disengaging the external access means for the multiple use universal connector, the cup-shaped portion of the diaphragm reseals itself for the reason that the membrane is resilient and springs back to its original configuration. As a result the container is resealed until the fluid withdrawal process is repeated.

We have found that both configurations of the M-shaped diaphragm perform well in resealing themselves in multiple use.

Figure 6:
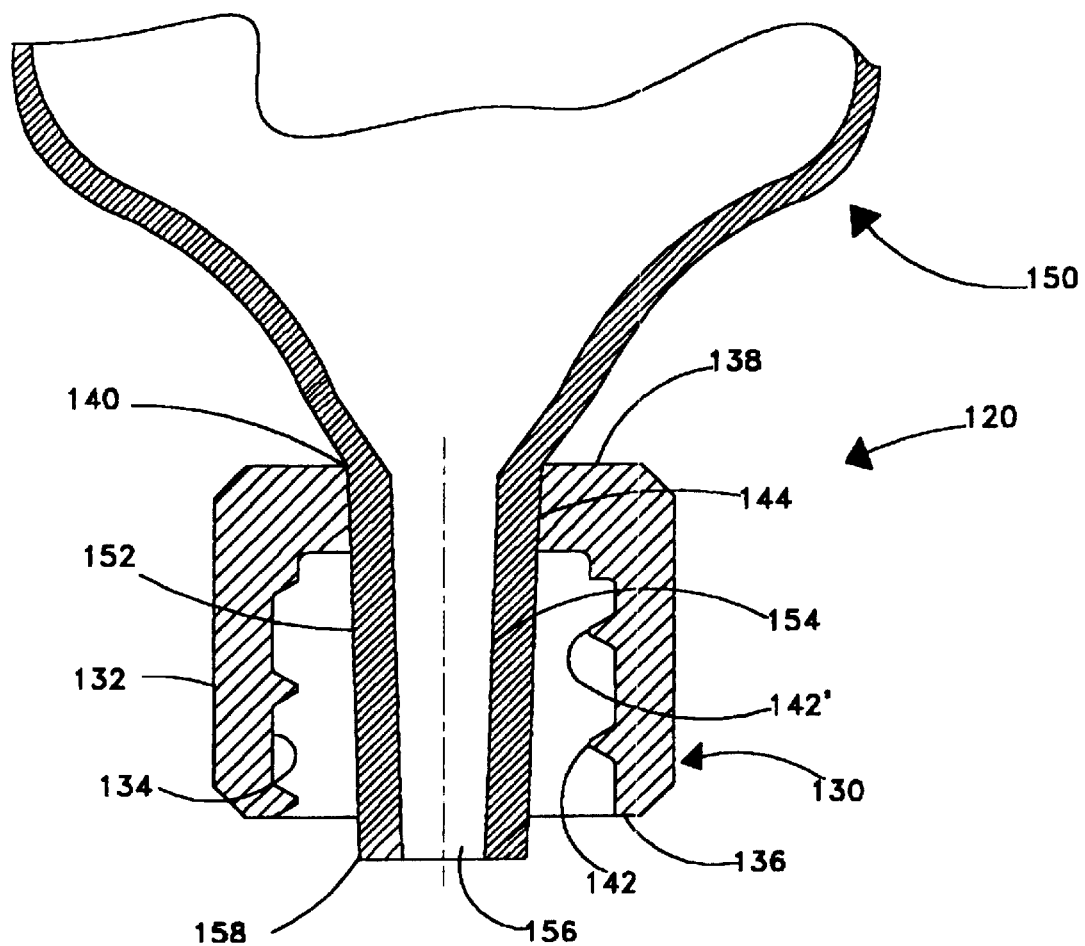
FIG. 6 is a cross-section of a luer connector attachable to the multiple use universal connector of the present invention.

FIG. 6 shows in cross-sectional view a luer connector attachable to each of the embodiments of the present invention. The luer connector 120 comprises a cylindrical cap 130 and tubing conduit 150. Cylindrical cap 130 closely approximates cylindrical cap 60 of the multiple use universal connector shown in FIGS. 3B and 3C and its function is to be threaded onto the multiple use universal connector when fluid communication is desired. Prior to threading cylindrical cap 130 of luer connector 120 onto the multiple use universal connector 30, cylindrical cap 60 is removed and then replaced by cylindrical cap 130 of luer-connector 120.

Cylindrical cap 130 of luer connector 120 comprises outside wall 132 and inside wall 134. Outside wall 132 comprises: bottom wall portion 136; top wall portion 138; and central portion 140 of top wall portion 138. Inside wall 134 comprises: internal threads 142 and 142' extending towards the center of the cap.

Tubing conduit 150 is positioned in cylindrical cap 130 of luer connector 120 at its top central portion 140. Thickened outside wall portion 144 parallelly faces outside wall 152 of tubing conduit 150 and is permanently attached thereto by adhesive or other suitable means known in the art. Tubing conduit further comprises: inside wall of tubing conduit 154 forming a fluid channel 156; and bottom end portion of tubing conduit 158 which extends beyond bottom portion 136 of cylindrical cap 130 of cylindrical cap of luer connector. When threaded onto multiple use universal connector 30, luer connector 120 travels towards second cap-locking ring 142, contacts diaphragm membrane 90 or 90' with its bottom and portion 158 and exerts pressure thereon in a twisting motion. The exerted force ruptures the elastomeric membrane thereby allowing fluid communication between the luer connector 120 and the content of the intravenous infusion bag.

The multiple use universal connector 30 and 30' may also be used in containers, such as bottles and vials the contents of which are intended to be accessed by a hypodermic syringe having either a sharp or blunt cannula. When fluid withdrawal or fluid addition is desired, cylindrical cap 60 or 60' of multiple use universal connector 30 or 30' is removed and the diaphragm is pierced by the cannula providing access to the content of the container or its withdrawal therefrom.

Figure 7A:
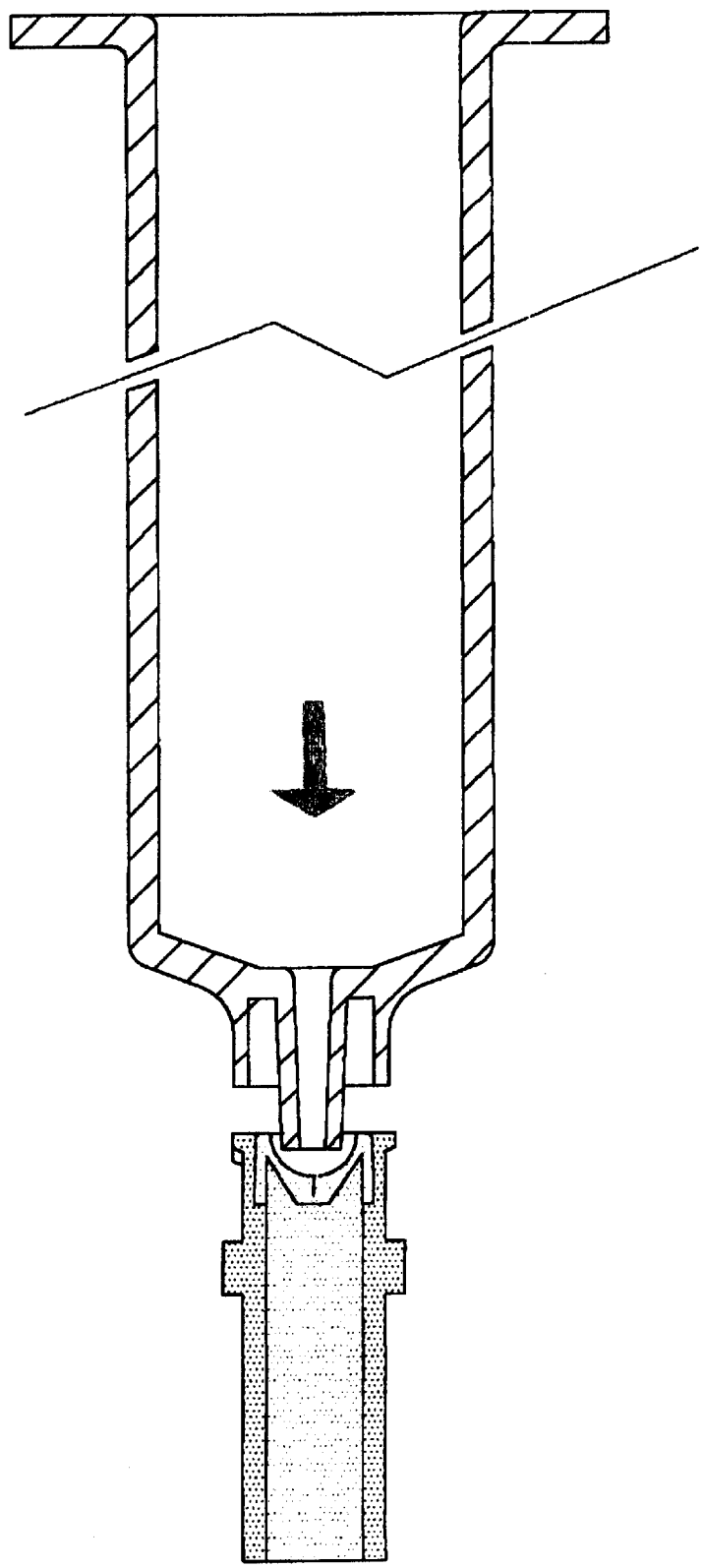
FIG. 7A is a cross-section of the multiple use universal connector prior to penetration of the diaphragm by the luer connector of a syringe.
Figure 7B:
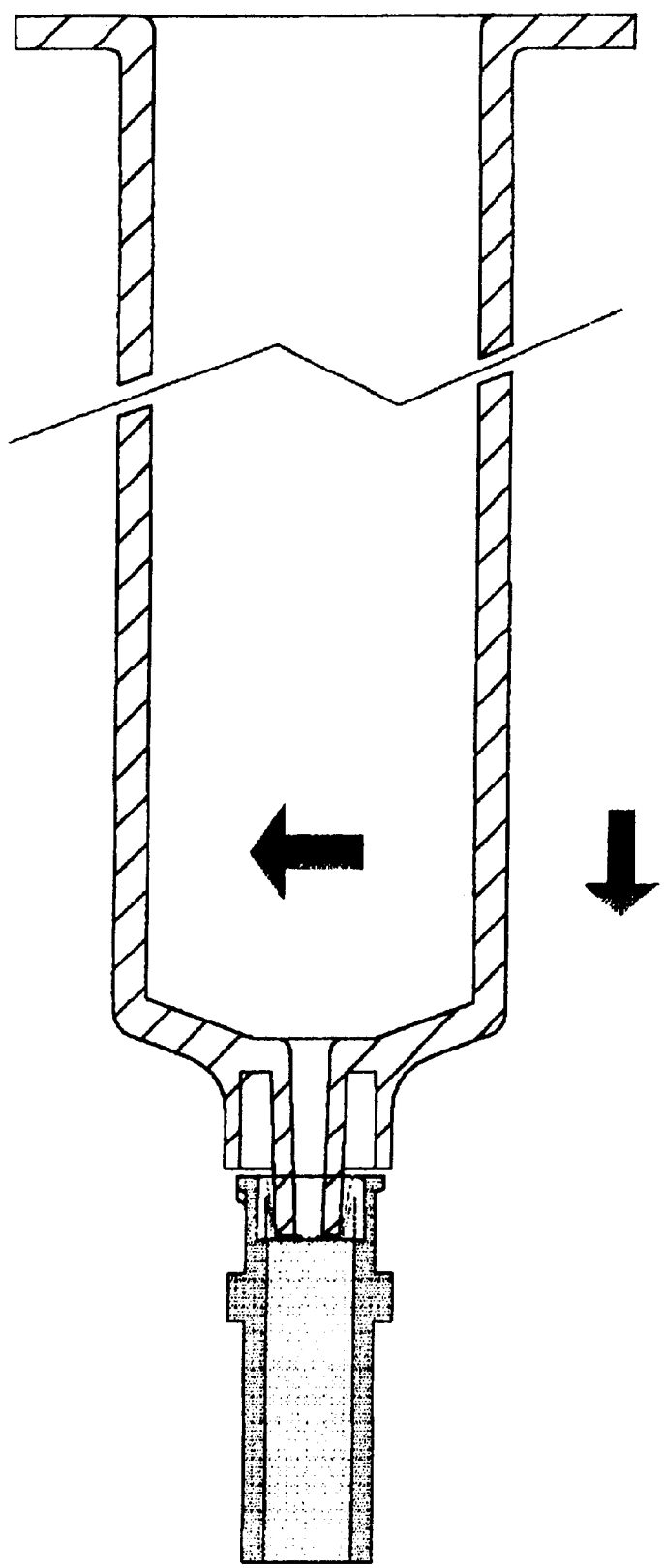
FIG. 7B is a cross-section of the multiple use universal connector at initial penetration and break-through of the diaphragm by the luer connector of a syringe.
Figure 7C:
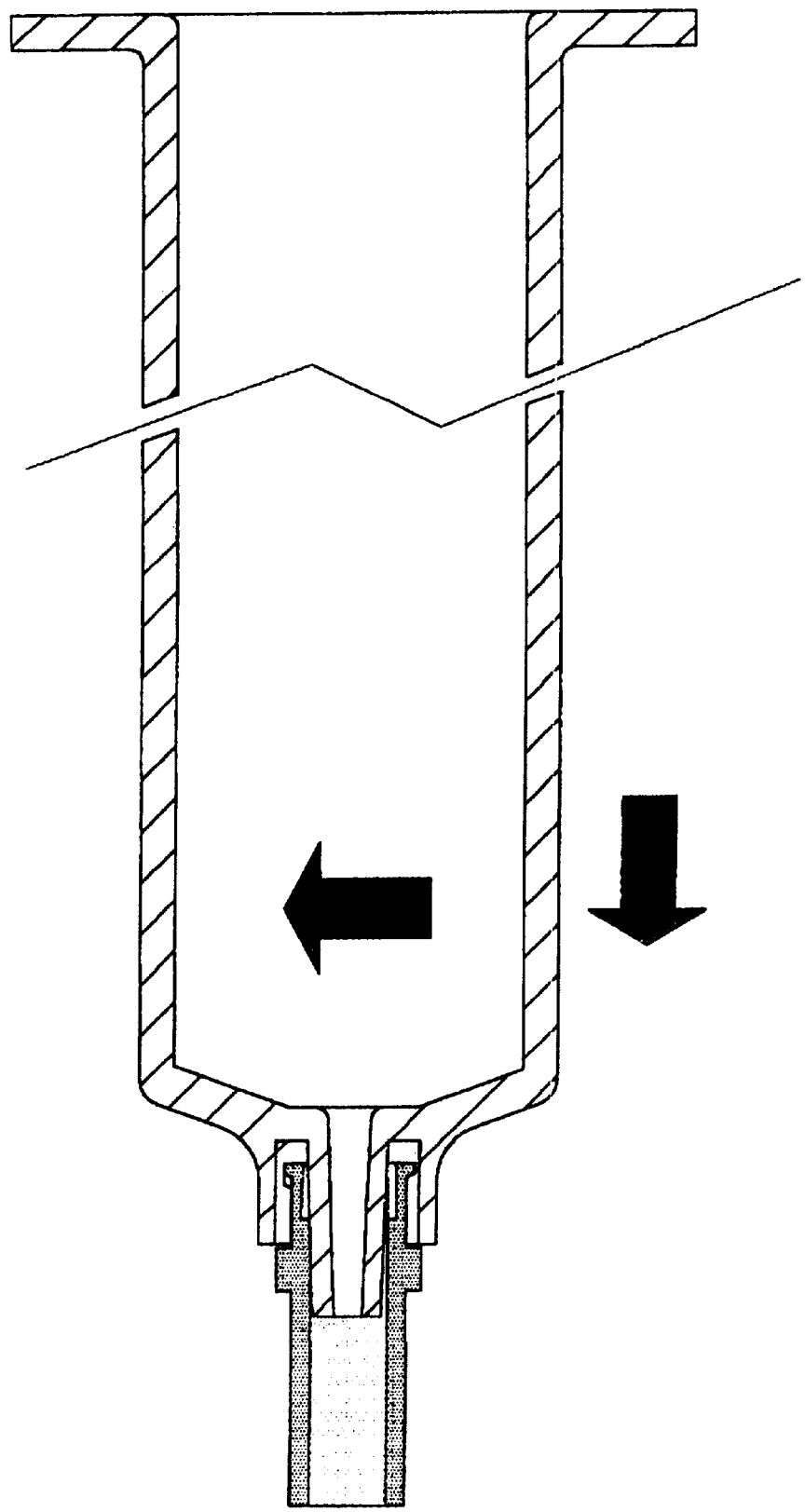
FIG. 7C is a cross-section of the multiple use universal connector at complete penetration of the diaphragm by a luer connector whereby full flow access of the content of the container is achieved.
Figure 7D:
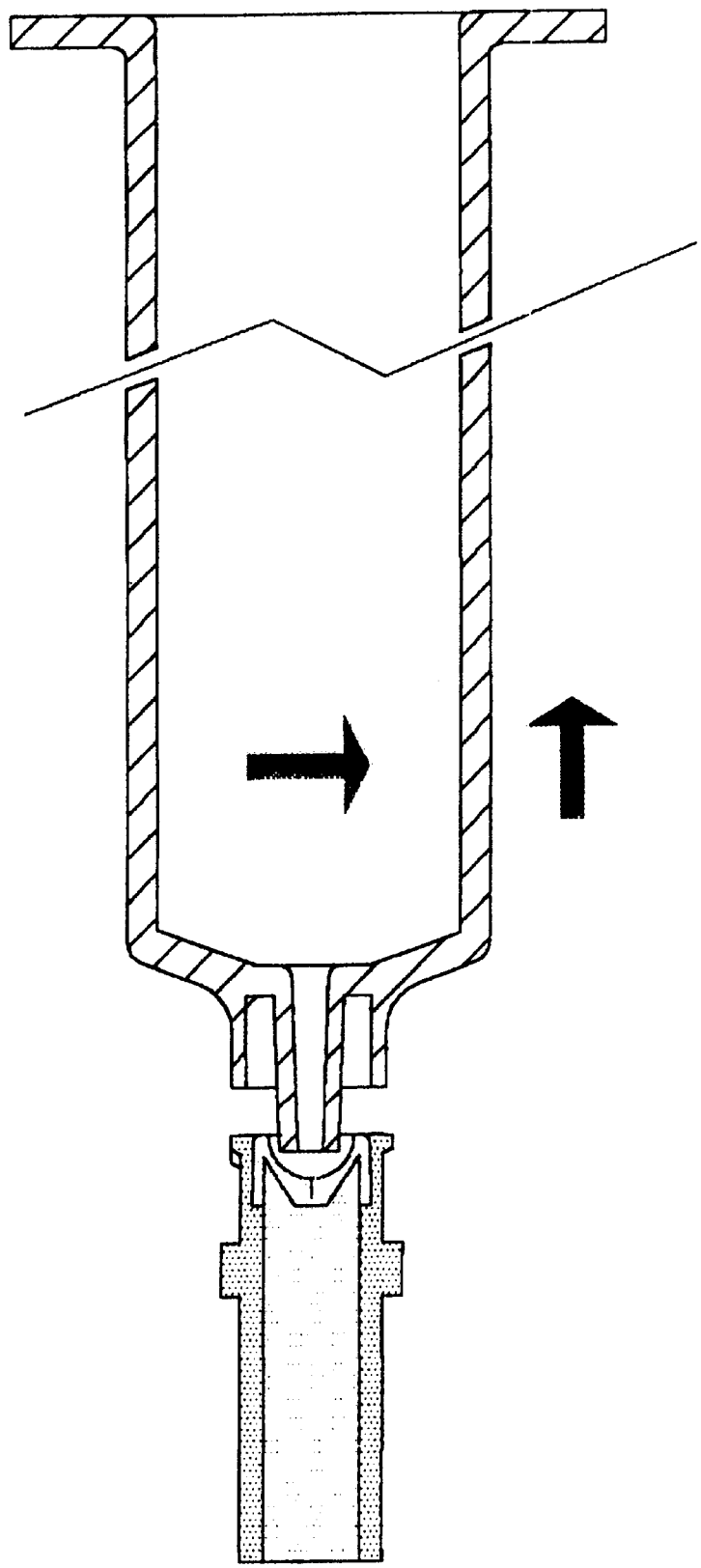
FIG. 7D is a cross-section of the multiple use universal connector after removal of a luer connector whereby the diaphragm reseals itself.

FIG. 7A is a cross-section of the multiple use universal connector prior to penetration of the diaphragm by the luer connector of a syringe;

FIG. 7B is a cross-section of the multiple use universal connector at initial penetration and break-through of the diaphragm by the luer connector of a syringe;

FIG. 7C is a cross-section of the multiple use universal connector at complete penetration of the diaphragm by a luer connector whereby full flow access of the content of the container (not shown) is achieved; and FIG. 7D is a cross-section of the multiple use universal connector after removal of a luer connector whereby the diaphragm reseals itself.

| | |
|---|---|
| Intravenous infusion bag (IV bag) | 10 |
| Fluid contained in bag | 12 |
| Fluid exit port or tube in IV bag | 14 |
| Distal end of fluid exit port or tube | 16 |
| Proximal end of fluid exit port or tube | 18 |
| Bottom seam of IV bag | 20 |
| Multiple use universal connector | 30, 30' |
| Distal end of multiple use universal connector | 32, 32' |
| Proximal end of multiple use universal connector | 34 |
| Inside wall of multiple use universal connector | 36 |
| Outside wall of multiple use universal connector | 38 |
| First cap-locking ring | 40, 40' |
| Proximal end of second cap locking-ring | 41, 41' |
| Second cap-locking ring | 42 |
| Distal end of inside wall of multiple use universal connector | 50 |
| Proximal end of inside wall of multiple use universal connector | 52, 52' |
| Side wall of cylindrical opening at proximal end of multiple use universal connector | 54 |
| Bottom wall of cylindrical opening at proximal end of multiple use universal connector | 56 |
| Cylindrical cap of multiple use universal connector | 60, 60' |
| Internal threads on cap | 66, 66' |
| Bottom wall of cap | 68, 68' |
| Top wall of cap | 70 |

-continued

| | |
|---|---|
| Plug | 71 |
| Central portion of top wall | 72 |
| Side wall of plug | 74 |
| Bottom wall of plug | 76 |
| Outside wall of cylindrical protuberance of cap | 78 |
| Bottom wall of cylindrical protuberance of cap | 80 |
| Shoulder connecting inside wall of cap and outside wall of cylindrical protuberance of cap | 82 |
| M-shaped diaphragm | 90, 90' |
| Leg portion of M-shaped diaphragm | 92, 92' |
| Cup-shaped portion of M-shaped diaphragm | 94, 94' |
| Horizontal bottom portion of cup-shaped portion | 96 |
| Side portion of cup-shaped portion | 98, 98' |
| Slit in bottom portion | 100, 100' |
| Top surface of horizontal bottom portion | 102 |
| Bottom surface of horizontal bottom portion | 104 |
| Unpenetrated membrane | 106, 106' |
| Luer connector | 120 |
| Cylindrical cap of luer connector | 130 |
| Top portion of cylindrical cap | 138 |
| Center top portion of cylindrical cap | 140 |
| Wall portion of cylindrical cap facing tubing conduit 150 | 144 |
| Tubing conduit in luer connector | 150 |
| Outside wall of tubing conduit | 152 |
| Inside wall of tubing conduit | 154 |
| Fluid channel | 156 |
| Bottom end portion of tubing conduit | 158 |

Various modifications of the present invention disclosed will become apparent. This invention is intended to include such modifications to be limited only by the scope of the claims.

What is claimed is:

1. A multiple use universal connector-container assembly comprising:
    a container having a fluid port; and
    a multiple use universal connector comprising:
    (1) a connector body of tube-like configuration having a distal end and a proximal end, wherein said distal end is slideably inserted and sealed into the fluid port of said container, and said proximal end is equipped with an elastomeric diaphragm and a removable cap;
    (2) said elastomeric diaphragm is of M-shaped configuration, capable of flexing under pressure, sealing the proximal end of said connector body, and being capable of re-sealing itself after being pierced by an external access means;
    (3) a first cap-locking ring on the proximal end of said connector body which serves as a male thread to receive said removable cap;
    (4) a second cap-locking ring, spaced from said first cap-locking ring towards the distal end of said connector body, which serves as stopping means for the removable cap;
    (5) said removable cap threaded onto the proximal end of said connector body to protect said elastomeric diaphragm from environmental forces and to maintain said elastomeric diaphragm in aseptic condition.

2. The multiple use universal connector-container assembly of claim 1 wherein said elastomeric M-shaped diaphragm comprises a leg portion and a cup-shaped portion and wherein said cup-shaped portion comprises a horizontal bottom portion having a top surface and a bottom surface, and a side portion which enclose an obtuse angle between them.

3. The multiple use universal connector-container assembly of claim 2 wherein said horizontal bottom portion comprises a slit extending from the top surface thereof toward the bottom surface thereof without penetrating said bottom surface.

4. The multiple use universal connector-container assembly of claim 2 wherein said cup-shaped portion comprises: a horizontal bottom portion having a top surface and a bottom surface, and a side portion which enclose a semicircular surface between them; and wherein said horizontal bottom portion comprises a slit extending from the top surface thereof toward the bottom surface thereof without penetrating said bottom surface.

5. A multiple use universal connector-medical container assembly comprising:
   a) a medical container having a medical fluid therein, said medical container comprises a fluid port for accessing the medical fluid contained therein or for transferring a medical fluid thereinto; and
   b) a multiple use universal connector comprising:
      (1) a connector body of tube-like configuration having a distal end and a proximal end, wherein said distal end is sealed into the fluid port of said medical container, and said proximal end is equipped with an elastomeric diaphragm and a removable cap;
      (2) said elastomeric diaphragm is of M-shaped configuration, capable of flexing under pressure, sealing the proximal end of said connector body, and being capable of re-sealing itself after being pierced by an external access means;
      (3) a first cap-locking ring on the proximal end of said connector body which serves as a male thread to receive said removable cap; and
      (4) a second cap-locking ring, spaced from said first cap-locking ring towards the distal end of said connector body, which serves as stopping means for the removable cap;
      (5) said removable cap threaded onto the proximal end of said connector body to protect said elastomeric diaphragm from environmental forces and to maintain said elastomeric diaphragm in aseptic condition.

6. The multiple use universal connector-medical container assembly of claim 5 wherein said elastomeric M-shaped diaphragm comprises a leg portion and a cup-shaped portion and wherein said cup-shaped portion comprises: a horizontal bottom portion having a top surface and a bottom surface; and a side portion which enclose an obtuse angle between them.

7. The multiple use universal connector-medical container assembly of claim 6 wherein said horizontal bottom portion comprises a slit extending from the top surface thereof toward the bottom surface thereof without penetrating said bottom surface.

8. The multiple use universal connector-medical container assembly of claim 6 wherein said cup-shaped portion comprises: a horizontal bottom portion having a top surface and a bottom surface; and a side portion which enclose a semicircular surface between them.

9. The multiple use universal connector-medical container assembly of claim 8 wherein said horizontal bottom portion comprises a slit extending from the top surface thereof toward the bottom surface thereof without penetrating said bottom surface.

10. A method of accessing a medical fluid contained in a medical container or introducing a medical fluid into a medical container equipped with a multiple use universal connector comprising the steps of:
   (A) providing a multiple use universal connector-medical container assembly comprising:
      a) the medical container having a fluid port and containing a medical fluid therein; and
      b) the multiple use universal connector:
         (1) a connector body of tube-like configuration having a distal end and a proximal end, wherein said distal end is sealed into the fluid port of said medical container, and said proximal end is equipped with an elastomeric diaphragm and a removable cap;
         (2) said elastomeric diaphragm is of M-shaped configuration, capable of flexing under pressure, sealing the proximal end of said connector body, and being capable of re-sealing itself after being pierced by an external access means;
         (3) a first cap-locking rind on the proximal end of said connector body which serves as a male thread to receive said removable cap;
         (4) a second cap-locking ring, spaced from said first cap-locking ring towards the distal end of said connector body; which serves as stopping means for the removable cap; and
         (5) said removable cap threaded onto the proximal end of said connector body to protect said elastomeric diaphragm from environmental forces and to maintain said elastomeric diaphragm in aseptic condition;
   (B) removing said removable cap from the proximal end of said connector body;
   (C) accessing the medical fluid contained in said container or introducing a medical fluid into said medical container by a luer connector which comprises;
      (a) a cylindrical cap having an inside wall; said inside wall having threads thereon and terminating in a bottom rim portion; and
      (b) a tubing conduit having a fluid channel therein contained in said cylindrical cap wherein an end of said tubing conduit extends beyond the bottom rim portion of said cylindrical cap and ruptures the elastomeric diaphragm as said cylindrical cap is threaded onto said universal connector to establish fluid communication with the medical fluid contained in said medical container or introducing a medical fluid into said medical container.

* * * * *